(12) United States Patent
Nielsen

(10) Patent No.: US 8,579,913 B2
(45) Date of Patent: Nov. 12, 2013

(54) DRIVE ASSEMBLY FOR FACILITATING DEPLOYMENT OF AN IMPLANTABLE MEDICAL DEVICE

(75) Inventor: Arne Mølgaard Nielsen, Copenhagen (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/369,911

(22) Filed: Feb. 9, 2012

(65) Prior Publication Data

US 2012/0209175 A1   Aug. 16, 2012

(30) Foreign Application Priority Data

Feb. 11, 2011 (GB) .................................. 1102460.1

(51) Int. Cl.
*A61F 2/06* (2013.01)
*A61F 2/84* (2006.01)

(52) U.S. Cl.
USPC .......................................... 606/108; 623/1.11

(58) Field of Classification Search
USPC ...................... 604/95.01, 207–216, 151–155; 606/108; 623/1.11; 128/DIG. 12, 128/DIG. 13
See application file for complete search history.

(56) References Cited

U.S. PATENT DOCUMENTS

| 2003/0028236 A1 | 2/2003 | Gillick et al. | |
| 2005/0090887 A1 | 4/2005 | Pryor | |
| 2009/0024137 A1* | 1/2009 | Chuter et al. | 606/108 |
| 2009/0270969 A1* | 10/2009 | Fargahi et al. | 623/1.11 |
| 2012/0029607 A1* | 2/2012 | McHugo et al. | 623/1.11 |

FOREIGN PATENT DOCUMENTS

| WO | 2005107644 A1 | 11/2005 |
| WO | 2009011866 A1 | 1/2009 |
| WO | 2009013642 A1 | 1/2009 |

\* cited by examiner

*Primary Examiner* — Nicholas Lucchesi
*Assistant Examiner* — Benjamin Koo
(74) *Attorney, Agent, or Firm* — Richard J. Godlewski

(57) ABSTRACT

A driver assembly (50) for an introducer assembly (10) for the deployment of an implantable medical device (16) includes a sprung element (52) coupled to a yoke (56). The yoke (56) is coupled to a gripper element (58). The yoke (56) is coupled to a first handle unit (30) of the introducer (10). The sprung element (52) is coupled to a proximal handle unit (32). A brake element (66) acts to prevent operation of the sprung element (52) when no manual force is being applied to attract a sheath (24) and the assembly (10). When manual retraction force is applied to the assembly (50) the gripper element (58) the brake element (66) releases a sprung element (52) so that the lighter can apply a force assistance to assist in the retraction of the sheath (24) and thereby to assist in the deployment of a medical device.

20 Claims, 8 Drawing Sheets

DRIVE ASSEMBLY FOR FACILITATING DEPLOYMENT OF AN IMPLANTABLE MEDICAL DEVICE

TECHNICAL FIELD

The present invention relates to a drive assembly for facilitating deployment of an implantable medical device.

BACKGROUND OF THE INVENTION

Implantable medical devices, such as stents, stent grafts, vena cava filters, occlusion devices, embolisation coils and so on, are often deployed endoluminally through a suitable percutaneous entry point of a patient. For instance, a medical device to be fitted within the aorta may be passed via the femoral artery, thus from an entry point a substantial distance from the treatment site.

The introducers used for the deployment of such devices tend to be elongate catheter assemblies in which the medical device is held at a distal end of the introducer in a radially compressed state until it is ready to be deployed. Typically, such introducer assemblies are formed from a plurality of components including one or more catheters, device restraining elements, guide wires and so on. The introducer also includes a covering sheath which covers the components of the introducer as well as the medical device.

Once the introducer has been inserted into a patient and the distal end thereof carrying the medical device located at the site of a patient's vasculature at which the device is to be positioned, the deployment mechanism is operated. The first stage of this is to pull back the outer sheath so as to expose the medical device, whereupon the constraining mechanism holding the medical device to the carrier catheter is then activated, normally in stages, to release the device. In some cases the device is releasable by self-expansion while in other cases a separate expansion mechanism, such as a balloon, is used.

In order to maintain the integrity of the components carried in the introducer, as well as to keep the outer diameter of the introducer, particularly at its distal end, as small as possible, the components of the assembly tend to be a relatively tight fit with one another. This relatively tight fit results in friction between the various slidable components of the assembly. To add to this, the proximal end of the device, that is the end which remains outside the patient during the procedure and which includes the various manual controls used by the clinician, is provided with at least one haemostatic valve or seal, often several, to prevent undesired loss of bodily fluids during the operation. There is necessarily provided a seal or valve between the covering sheath and the inner catheter or catheters to prevent fluid leakage from the space between these components. Such seals tend to contribute to friction between the various sliding components of the device and thus to an increased required operation force.

Moreover, introducer devices of this nature tend to be very long, an introducer for a medical device to be implanted in the aorta or heart typically having a length of at least 1.5 metres. Furthermore, the path such introducers have to follow through a patient's vasculature is normally tortuous, such that they have to curve and often twist along their length. Such curvature and twisting also adds to the friction between the slidable components of the assembly.

The above-mentioned factors lead to it being necessary for the clinician to apply a substantial force to the assembly in order, in particular, to pull the outer sheath back so as to expose the medical device. Having to use a large force to operate the assembly can cause practical difficulties, not only in the effort which the clinician must expend in operating the device, but also in augmenting the risk of the introducer assembly, particularly its distal end, moving unintentionally out of position. Any such movement can lead to incorrect positioning of the medical device. Furthermore, in the case of a device which is rotationally dependant, such as a fenestrated or branched stent graft, for example, any shifting of the introducer can cause rotational misalignment. In order to seek to mitigate these problems, the clinician may need to carry out positional adjustments to the assembly at the same time as effecting the various steps required to deploy the device, which is a complex and time consuming task. At worst, the device cannot be properly deployed and the procedure must be aborted.

There are devices which effect the deployment of the medical device, in particular retraction of the outer sheath, automatically, for instance by means of a sprung loaded and trigger actuated handle assembly. Some rotary handles are known which use a screw mechanism to overcome the longitudinal pulling force; as well as ratchet type handles. These devices can overcome the difficulties indicated above, by providing what could be described as motorised assistance, allowing the clinician to maintain accurate control of the positioning of the introducer while the device exerts the effort required to retract the sheath.

However, in many instances clinicians do not wish to lose the manual control of the operation of the introducer assembly as this can lead to a loss of the fine adjustments clinicians often desire during deployment of the medical device. For instance, a clinician may wish to slow or even temporarily stop the withdrawal of the sheath part way in order to carry out a fine adjustment of the position or orientation of the medical prosthesis. An automatic deployment device may not provide for this. Furthermore, a manually operated introducer gives the clinician tactile feedback as to how the deployment is progressing, whereas an automatic deployment mechanism will generally fail to provide such feedback, causing the clinician to have to rely upon imaging only.

As a result, it in some circumstances it is preferred to retain manual operation of the introducer, despite the problems associated with this.

SUMMARY OF THE INVENTION

The present invention seeks to provide an improved introducer assembly and drive assembly for an introducer.

According to an aspect of the present invention, there is provided an introducer assembly including a carrier element for carrying an implantable medical device, the carrier element including a distal end at which an implantable medical device is carried and a proximal end; a sheath overlying the carrier element and being retractable so as to expose the distal end of the carrier element, the sheath including a distal end and a proximal end; a handle assembly at the proximal end of the carrier element and sheath, the handle assembly being manually operable to retract the sheath; and a drive assembly coupled between the carrier element and the sheath and operable to provide a retraction assistance force upon manual retraction of the sheath.

An introducer having such a structure retains the manual operation and tactile feel not provided with automatic actuator systems, yet provides mechanical assistance in order to avoid the problems of existing manually operable introducer assemblies.

In an embodiment, the handle assembly includes first and second handle portions, attached respectively to the proximal ends of the sheath and the carrier element. The two handle portions can be held by a clinician and pulled in a direction towards one another so as to retract the sheath from the distal end of the carrier element and thereby to expose a medical device carried thereon.

In this embodiment, the drive means is coupled between the first and second handle portions and acts to provide a force pulling these handle portions together. In the preferred embodiment, the sprung element is coupled between the handle portions.

More generally, the drive assembly preferably includes a sprung element coupled to the sheath and operable to pull the sheath in a retraction direction.

The sprung element may in some embodiments provide a retraction force which is insufficient to pull back the sheath without manual assistance. In other embodiments, as described below, the sprung element may generate a force sufficient to pull back the sheath, in which case there would be provided a control mechanism to ensure retraction of the sheath only when desired.

In the preferred embodiment, the drive assembly includes a brake element operable to prevent retraction of the sheath until the sheath is manually pulled back by the user. In a practical embodiment, the brake element adopts a braking condition when there is no manual actuation of the handle assembly and a released condition when there is manual operation of the handle assembly. Preferably, the brake acts to prevent operation of the sprung element.

It is preferred that the drive assembly provides mechanical assistance up to a threshold retraction rate, beyond which the only effective retraction force is from manual actuation of the handle assembly. In the preferred embodiment, this is by means of the drive assembly having a sprung element which has a limited return speed, that is a limited speed by which it returns to its not stressed condition. This may be achieved by an inherent dynamic limitation in the sprung element or by means of a damper, for instance.

The sprung element is preferably a spiral spring, preferably of a type similar to a watch or clock spring. Such a spring can be fitted to a spool element and the brake means can be designed to act upon the spool element so as to stop this from rotating and thereby to stop the spring from moving the handle portions towards one another. The brake element can be releasable upon manual movement of the handle portions. In this regard, the drive assembly preferably includes a brake release mechanism operable to release the brake upon manual pulling of the handle portions together. The brake release mechanism may operate on the basis of the speed of manual retraction, thereby providing controlled force assistance. If manual retraction is too slow the brake engages again, thereby ensuring that the clinician never loses control of the operation of the introducer.

BRIEF DESCRIPTION OF THE DRAWING

Embodiments of the present invention are described below, by way of example only, with reference to the accompanying drawings, in which.

DETAILED DESCRIPTION

It is to be understood that the Figures are schematic and do not show the various components in their actual scale. In many instances, the Figures show scaled up components to assist the reader.

In this description, when referring to a deployment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

Figure 1:
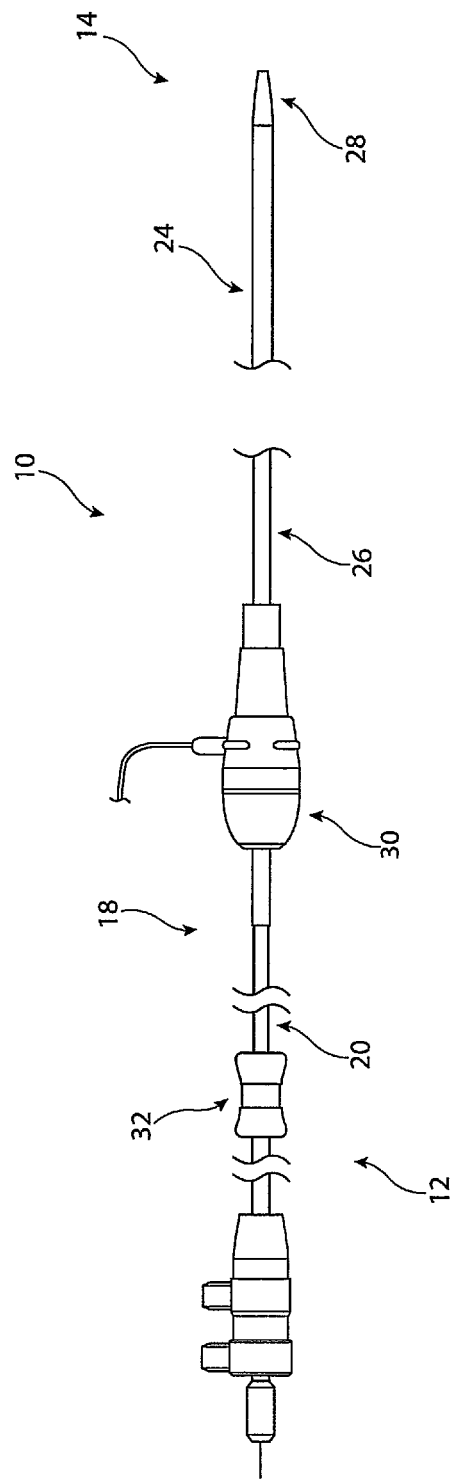
FIG. 1 shows an example of the proximal end of a prior art introducer assembly.
Figure 2:
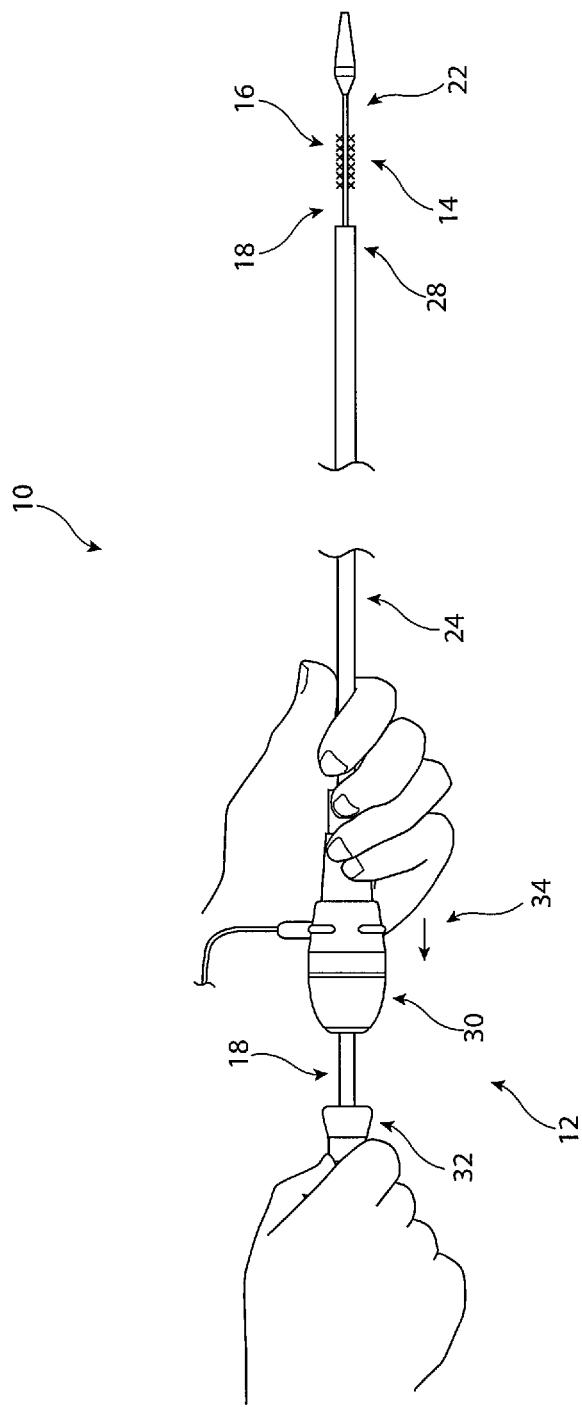
FIG. 2 shows in schematic form the primary components of a preferred embodiment of introducer assembly incorporating a drive assembly.

Referring to FIG. 1, there is shown an introducer assembly 10 designed for deploying implantable medical devices within the lumen of a patient. The assembly 10, of which only the principal components are shown, has a proximal end 12 which remains outside the patient during the medical procedure and a distal end 14 which during the procedure is located within a patient's vasculature or other organ. The distal end 14 carries, in this example, an implantable medical device 16, as shown in FIG. 2.

The introducer assembly 10 includes a carrier element or catheter 18 which has a proximal end 20 at the proximal end 12 of the assembly and a distal end 22 at the distal end 14 of the assembly 10. The carrier element 18 carries, at its distal end, an implantable medical device 16 and is typically provided with restraining mechanisms for holding the medical device 16 in a radially constrained configuration, as well as one or more lumens for guide wires, flushing fluid and so on. The structure of the carrier element 18 can be of a type well known in the art and therefore is not described in detail herein.

Located over the carrier element 18 is a sheath 24, which has a proximal end 26 and a distal end 28 which extends up to the distal end 14 of the introducer 10. Prior to deployment of the medical device 16, the distal end 28 of the sheath 24 covers all or most of the distal end of the carrier element 18 and in particular covers the medical device 16, as will be apparent from a comparison of FIGS. 1 and 2.

The proximal ends 26, 20 of the sheath 24 and carrier catheter 18 are attached, respectively, to first and second handle units 30, 32. As is conventional with known introducer assemblies, the handle units 30, 32 include haemostatic valves, flushing ports, possibly one or more device release mechanisms and so on. As such features are well known in the art they are not described in detail herein.

The conventional manner of operating the introducer assembly of FIG. 1 can be seen with reference to FIG. 2.

The clinician holds the two handle portions 30, 32 with two hands and pulls back the sheath by pulling back the handle 30 relative to the handle unit 32, in the direction of the arrow 34. This action causes the distal end 28 of the sheath 24 to be retracted relative to the distal end 22 of the carrier catheter 18, so as to expose the medical device 16. As the skilled person will know, this operation is carried out once the introducer assembly 10 has been satisfactorily positioned within a patient, such that the distal end 14 of the introducer assembly 10 is located at the site at which the implantable medical device 16 is to be deployed. Up to that point, the distal end 28 of the sheath 24 is retained in its covering position, that is to overlie the medical device 16.

For the reasons explained above, it can take substantial effort for the clinician to pull back the handle unit 30, particularly at the commencement of the deployment procedure. This effort can lead to unintentional jolting or shifting of the introducer assembly 10 and thus to the medical device 16 being displaced. Any such shifting would require repositioning of the medical device once the sheath 24 has been retracted and thus once the medical device is at least partially exposed. In a worst case situation the procedure might have to be aborted.

Figure 3:
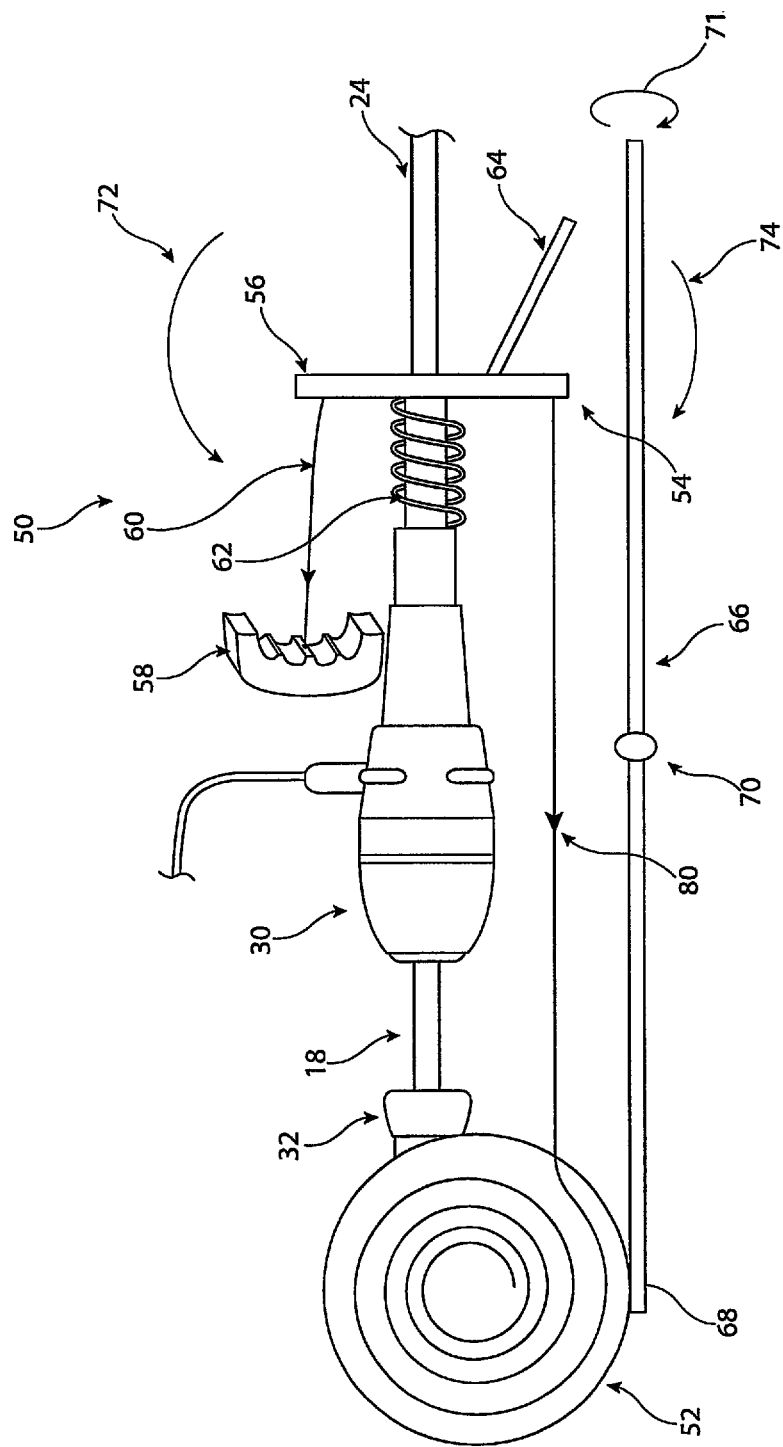
FIG. 3 shows detail of the drive assembly of FIG. 2.

Referring now to FIG. 3, there is shown a preferred embodiment of drive assembly 50, coupled between the carrier element 18 and the sheath 24. The drive assembly 50 is designed to provide retraction assistance force upon manual retraction of the sheath. The drive assembly 50 is, in this embodiment, coupled to the handle portions 30, 32 of the sheath 24 and carrier element or catheter 18, respectively.

Figure 4:
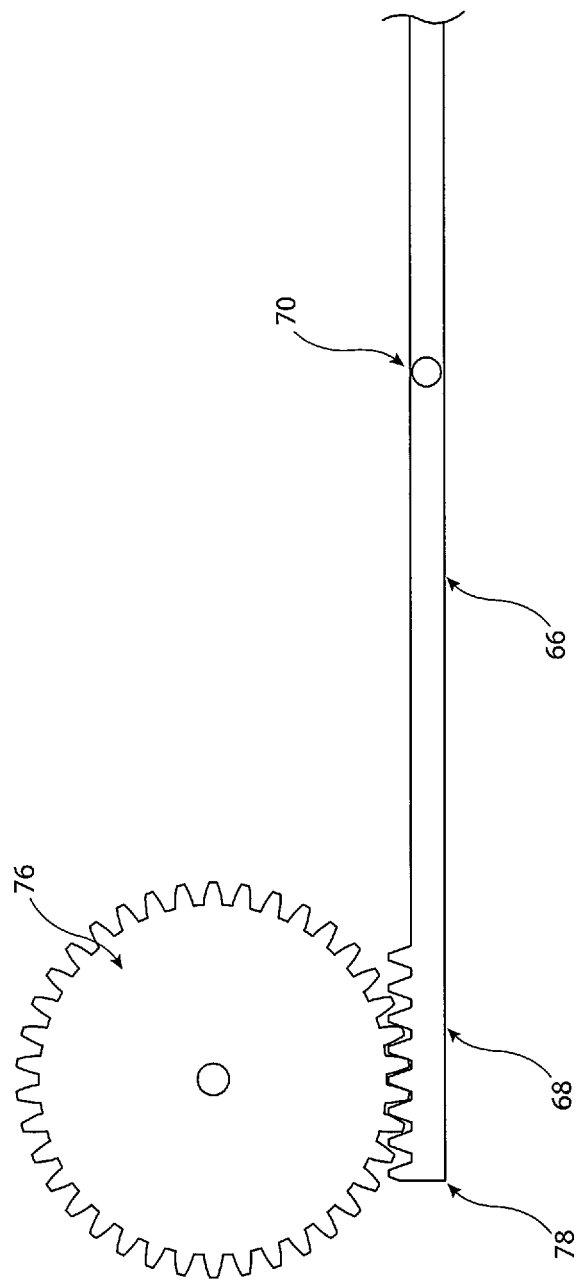
FIG. 4 shows in schematic form an embodiment of brake mechanism for the assembly of FIG. 3.

The retraction force of the drive assembly 50 is provided, in this embodiment, by means of a spiral spring 52, which is supported on a reel or spool, of which an embodiment is shown in FIG. 4 and described below. The spring element 52 is attached at one end 54 to a yoke 56 which is fitted over the sheath 24 just distal of the handle unit 30. For this purpose, the yoke 56 includes a hole or bore therein (not shown) through which the sheath 24 can pass. The support for the sprung element 52 (of which an embodiment is shown in FIG. 4) is connected to the handle unit 32 in such a manner that a clinician can still hold in one hand the handle unit 32 (or any other component which is directly connected to the handle unit 32).

At the yoke 56, there is provided a gripping element 58 which, in this embodiment, is attached to the yoke 56 by means of a tether 60. The yoke 56 acts upon the handle unit 30 through a coil spring 62, which is held at one end by the yoke 56 and at its other end against the handle unit 30 (for this purpose, there may be provided a suitable stop element, for example a washer between the handle unit 30 and the end of the coil spring 62).

Also attached to the yoke 56 is a brake release element 64 which, as described below, acts with the yoke, the gripper 58 and sprung element 52. Adjacent the brake release element 64 is a brake element 66, which has a proximal end 68 able to engage the mechanism of the sprung element 52 so as to stop this from imparting a pulling force on the yoke 56, thereby on the handle unit 30, in a manner described in detail below. The brake element 66 is pivotable about a pivot point 70. The pivot point 70 preferably allows the brake element 66 to tilt sideways relative to its longitudinal axis, as described in further detail below.

As shown by the arrows 72, 74, the yoke 56 is able to tilt to a certain extent on the sheath 24, in dependence upon the magnitude of the forces applied to it by the sprung element 52 and by the grip element 58 (that is by the clinician).

Referring now to FIG. 4, there is shown in schematic form an example of brake mechanism for the assembly shown in FIG. 3. The spiral spring 52 is fitted to a toothed spool 76, with the coiled end of the spring 52 fixed into a suitable support (not shown) of the spool 76. The brake element 66 is provided at its end 68 with a toothed region 78 able to engage the teeth of the spool 76. Thus, when the brake element 66 is biased towards the spool 76 its teeth will engage the teeth at the spool element 76 so as to stop this from rotating, thereby to stop the sprung element 52 imparting any further pulling force on the yoke 56 and thus upon the handle unit 30.

It will be apparent to the person skilled in the art that the assembly 50 shown in FIG. 3 (as with the mechanism shown in FIGS. 4 and 5 to 9 described in further detail below) will be provided on a frame or housing to support the various components. Such frame or housing will be dependent upon the design of the final form of the assembly 50, as well as dependent upon user preference. The design of such a housing or support frame is well within the capabilities of the skilled person and it is therefore not considered necessary to describe a particular housing in order to illustrate the principles of the invention taught herein.

Not shown in FIG. 3 or 4 is the provision of a weak spring which tends to bias the brake element 66 into a released position (that is to be biased to rotate in an anti-clockwise direction in the view of FIG. 3), in order to facilitate the release of the driver means and in particular the function of the sprung element 52.

When there is no manual actuation of the introducer, that is in the condition shown in FIG. 3, the force of the sprung element 52 will tend to pull the yoke 56 in the direction of the arrow 74, thereby causing the brake release element 64 to press upon the brake element 66, which thereby causes this to pivot (and rotate) about the point 70, resulting in the end 68 of the brake element 66 engaging the spool of the sprung element 52 so as to prevent the sprung element 52 from imparting any further pulling force upon the handle unit 30. The spring 62 upon which the yoke 56 is mounted enables the sprung element 52 to impart a tilting force upon the yoke 56 to cause this to engage the brake element 66 but not a force which is sufficient to overcome the spring 62 and thereby to move the handle unit 30 towards the handle unit 32.

The yoke 56 will remain in the tilted position, with the release element 64 pressing against the brake element 66, until manual actuation of the drive element of the assembly 50.

In order to retract the sleeve 24, that is to pull the handle unit 30 backwards towards the handle unit 32, the clinician will grasp onto the gripper element 58 and the handle 32 and pull the gripper element 58 in a proximal direction (that is towards the handle unit 32). The motion is analogous to that of FIG. 2. Thus, in terms of operation, the only difference between the arrangement in FIG. 2 and the embodiment of FIG. 3 is that the clinician will hold the gripper 58 rather than the handle unit 30.

Pulling on the gripper unit 58 will cause the yoke 56 to tilt in the direction of arrow 72, thereby to cause the release element 64 to move away from the brake element 66. When this occurs, in particular with the aid of the weak spring described above, the brake element 66 will rotate so that its end 68 disengages from the mechanism of the sprung element 52, thereby enabling the sprung element 52 to impart a pulling force upon the yoke 56. The pulling force is in the direction of the arrow 80 shown in FIG. 3.

The pulling force provided by the sprung element 52 assists in the retraction of a sheath 24, thereby to provide mechanical assistance to the effort expended by the clinician in pulling the handle 58. In other words, the spring 52 acts to provide an additional retraction force, thereby reducing the amount of effort which the clinician needs to apply to the introducer assembly 10. This assistance reduces the risk of the clinician jolting or otherwise undesirably moving the introducer assembly 10 during the deployment procedure and thereby reduces the risk of the distal end 14 of the assembly 10 being moved so as to become displaced in the patient's vasculature. At the start of the operation the spring 52 will provide a greater pulling force compared to the force it will produce towards the end of its rotational travel. This greater initial force is useful in overcoming the greater frictional forces experienced at the start of pulling back of the sheath 24.

Should the force applied by the clinician on the gripper element 58 be insufficient, that is should the clinician pull the gripper element 58 backwards too slowly, the sprung element 52 will pull at a greater speed, thereby tilting the yoke 56 in the direction of the arrow 74, to cause the release element 64 to re-engage the brake element 66 and stop further assistance by the sprung element 52. Therefore, the assistance provided by the sprung element 52 will only occur while the clinician is pulling the gripper element 58 at at least the same speed as the speed of retraction provided by the sprung element 52. This provides retraction control. As described below, the soft braking function of the brake element 66 and pad 114 can provide advantageous speed control for the physician.

By contrast, in some embodiments which use a speed limiter such as a damper or spool 76, should the clinician pull the gripper element 58 backwards at a rate faster than the rate of operation of the spring 52, the spring 52 will no longer provide any effective or noticeable force assistance. Thus, pulling the gripper element 58 by more than the threshold operating rate of the spring 52 will in effect remove the mechanical assistance which is otherwise generated by the sprung element 52.

This combination of effects provides a control to the amount and nature of the mechanical assistance (the force assistance) which is generated by the assembly 50. Moreover, given the braking feature of the assembly 50, the clinician remains in complete control of the deployment operation, including factors such as speed of retraction of the sheath 24, in a manner which is not possible with some fully automated systems. Specifically, should the clinician pull the gripper element 58 too slowly, the brake will continue to be engaged in a repetitive manner, whereas if the clinician pulls at a median rate there is full force assistance from the sprung element 52, while if the clinician pulls at a faster rate than the operating rate of the spring 52, there will be no force assistance.

The arrangement and operation of the drive assembly 50 could be described as to provide servo assistance to the introducer 10.

Figure 5:
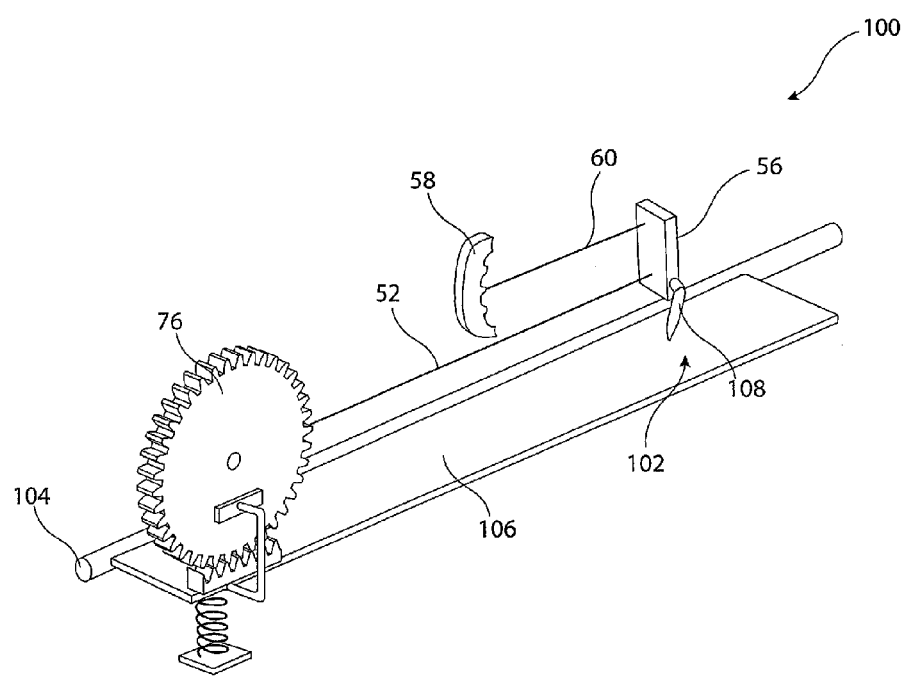
FIGS. 5 and 6 show in detail a preferred embodiment of drive assembly which includes a speed control function.
Figure 6:
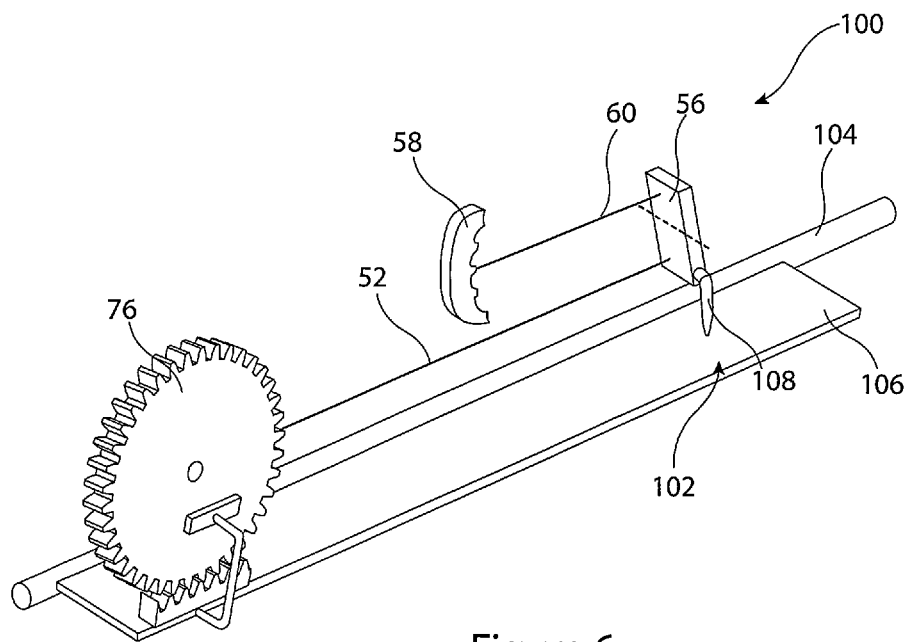

Referring now to FIGS. 5 and 6, there is shown an embodiment of brake mechanism which includes a speed control function in addition to a brake function. The assembly 100 of this embodiment makes use of the yoke 56 previously described and toothed wheel 76 supporting the spiral spring 52. The additional features relate to the brake and speed control assembly 102. The assembly includes a pivotable and twistable control rod 104 to which is attached an elongate flange or wing 106. Resting on and slidable along the flange 106 is a contact arm 108 which is coupled to the yoke 56, in practice to rotate the rod 104.

Coupled to the flange 106, at the toothed wheel location, is a resilient arm 110 which extends, in this embodiment, substantially perpendicularly from the flange 106 and it has attached thereto a foot 112 which carries a brake pad 114. Brake pad 114 may be a friction element of conventional form, one example being rubber or a rubberlike material.

A spring 116 is provided at what could be termed with respect to the drawings on the underside of the flange 106 and is held by a suitable support 118, which would typically be part of the casing or frame of the assembly. The spring 116 biases the flange 106 towards the toothed wheel 76, in practice in a braking and locking configuration. Spring 116 is of a strength that it is sufficient to cause braking of the mechanism when no external forces are applied thereto but which is overcome when the handle 58 is pulled in the normal course of deployment, as described herein.

Figure 7:
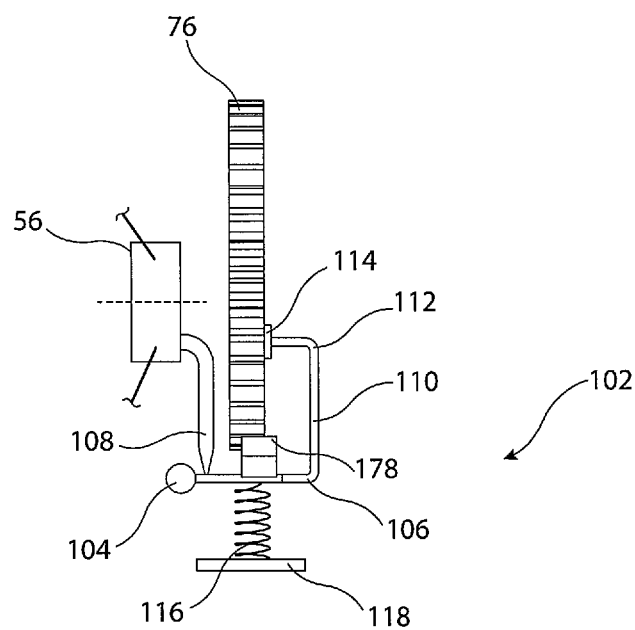
FIGS. 7 to 9 show the drive assembly of FIGS. 5 and 6 in three different modes of operation.
Figure 8:
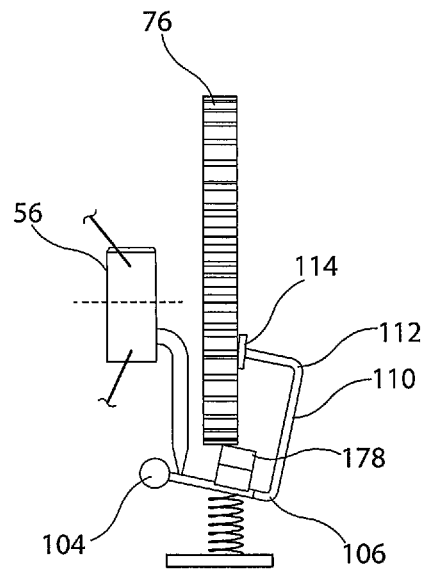
Figure 9:
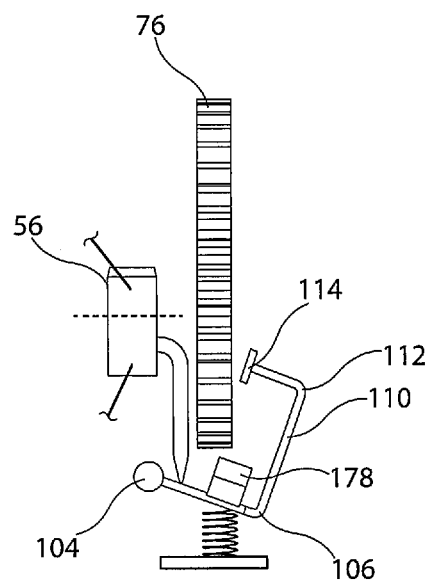

Referring in particular to FIGS. 7 to 9, the mechanism 100 is shown in three different operating conditions. In FIG. 7, there is no external force applied to the mechanism 102 by the yoke 56; that is, the handle 58 is not being operated by the clinician and the spring 116 is therefore able to cause the speed control brake pad 114 to engage the toothed wheel 76 as well as the toothed ratchet 178 at the end of the flange 106.

FIG. 8 shows a condition in which the yoke 56 is only partially tilted, as a result of pulling of the handle 58 at only an intermediate rate, which is sufficient to rotate the rod 104 and therefore the flange 106 enough to disengage the teeth 178 from the toothed wheel 76 which still results in application of the brake pad 114 against the side of the toothed wheel 76. This controls the speed of rotation of the toothed wheel 76 and therefore the speed of retraction of the sheath 24. The force of the brake pad 114 against the toothed wheel 76 can be adjusted by increasing or reducing the speed of pulling on the handle 58 within this intermediate range, thereby to control the speed of rotation of the toothed wheel 76 thereby the speed of retraction of the sheath 24.

In FIG. 9 the yoke 56 is fully tilted, causing also disengagement of the brake pad 114, thereby allowing unrestricted rotation of the toothed wheel 76 under the force of the coil spring 52. This will typically occur when the handle 58 is pulled at the same speed as the speed of contraction produced by the coil spring 52.

Abutment of the brake pad 114 against the side of the spool 76 generates a frictional braking force able to impart a gradual braking of the spool 76 and thus of the spring assistance on the assembly. This can give the brake 66 a soft braking function to slow the handle gradually. This can also provide an element of speed control in a manner similar to using a car's brake to control the speed of the car.

It will be appreciated that the preferred embodiment of brake mechanism 66 provides both braking by the brake pad 114 and by engagement of the teeth 78.

Figure 10:
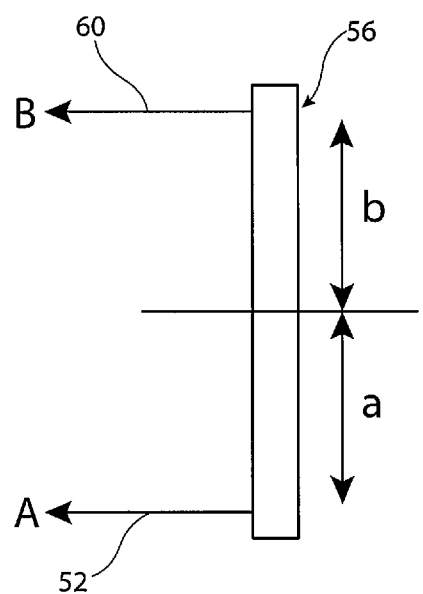
FIG. 10 shows in schematic form a force ratio balancing scheme for the yoke 56.

Referring now to FIG. 10, there is shown in schematic form a scheme for adjusting the force ratio of the assembly, via the yoke 56. Linear force B (applied by the handle 58) is determined in terms of its moment of force by the distance b relative to the pivot point of the yoke 56. Similarly, force $\overline{A}$ provided by the spring 52 is determined by the distance a $\overline{to}$ the pivot point of the yoke 56. Thus, manual force B×length b is balanced over the yoke pivot point with respect to servo force A×distance a. During movement these two moments will be balanced and if they are not the brake will be engaged or disengaged until the balance is restored. The required pulling force can be adjust by adjusting the ratio of a to b, that is by adjusting the relative distances between the points of pulling of 60 or 52 on the pivot point of the yoke 56. Such adjustment can be provided in a manner which can be effected by the clinician or factory set as preferred.

The drive assembly disclosed herein can be used with existing designs of manually operated introducer assemblies, for instance for the applicant's Zenith endovascular graft. The drive assembly could, therefore, be provided also as a device which can be fitted as a retrofit item to a conventional manually operated introducer assembly.

What has been described and illustrated herein is a preferred embodiment of the invention along with some of its variations. The terms, descriptions and Figures used herein are set forth by way of illustration only and are not meant as limitations. Those skilled in the art will recognize that many variations are possible within the scope of the claims.

What is claimed is:

1. An introducer assembly including a carrier element for carrying an implantable medical device, the carrier element including a distal end at which an implantable medical device is carried and a proximal end;
   a sheath overlying the carrier element and being retractable so as to expose the distal end of the carrier element, the sheath including a distal end and a proximal end;
   a handle assembly at the proximal end of the carrier element and sheath, the handle assembly including first and second handle portions, attached respectively to the proximal ends of the sheath and the carrier element, the handle assembly being manually operable to retract the sheath by pulling the first and second handle portions towards one another;
   and a drive assembly coupled between the first and second handle portions and operable to provide a retraction assistance force pulling the first and second handle portions together; wherein the drive assembly includes a brake element configured to prevent the drive assembly from providing the retraction assistance force when there is no manual actuation;
   a yoke fitted over the sheath;
   a sprung element attached to the yoke;
   a brake release element attached to the yoke and releasable engaged to the brake element;
   the sprung element imparting a pulling force on the yoke, thereby placing the yoke in a tilted position relative to the sheath; and
   wherein when the yoke is in the tilted position, the brake release element engages the brake element so that the brake element prevents the drive assembly from providing the retraction assistance force.

2. An introducer assembly according to claim 1, wherein the sprung element is a spiral spring.

3. An introducer assembly according to claim 2, wherein the spring is fitted to a spool element, the brake element being configured to act upon the spool element to prevent the spring from pulling the sheath in a retraction direction.

4. An introducer assembly according to claim 1, wherein the brake element is operable to prevent retraction of the sheath until the sheath is manually pulled back by the user.

5. An introducer assembly according to claim 4, wherein the brake element adopts a braking condition when there is no manual actuation of the handle assembly and a released condition when there is manual operation of the handle assembly.

6. An introducer assembly according to claim 4, wherein the brake element acts to prevent operation of the sprung element.

7. An introducer assembly according to claim 1, wherein the drive assembly includes a brake release mechanism operable to release the brake element upon manual pulling of the handle portions together.

8. An introducer assembly according to claim 7, wherein the brake release mechanism operates on the basis of the speed of manual retraction.

9. An introducer assembly according to claim 1, wherein the drive assembly provides mechanical assistance up to a threshold retraction rate.

10. An introducer assembly according to claim 9, wherein the drive assembly includes a sprung element which has a limited return speed.

11. An introducer assembly according to claim 1, including a speed control mechanism.

12. An introducer assembly according to claim 11, wherein the speed control mechanism includes a friction element for applying friction to the drive assembly thereby to control its speed of movement.

13. A drive assembly and an introducer assembly including a carrier element for carrying an implantable medical device, the carrier element including a distal end at which an implantable medical device is carried and a proximal end; a sheath overlying the carrier element and being retractable so as to expose the distal end of the carrier element, the sheath including a distal end and a proximal end; a handle assembly at the proximal end of the carrier element and sheath and including first and second handle portions, attached respectively to the proximal ends of the sheath and the carrier element, the handle assembly being manually operable to retract the sheath by pulling the first and second handle portions towards one another; wherein the drive assembly is able to be coupled between the carrier element and the sheath and operable to provide a retraction assistance force in response to manual retraction of the sheath; the drive assembly including:
   a brake element operable to prevent retraction of the sheath until the sheath is manually pulled back by the user and to prevent a sprung element from providing the pulling force if there is no manual actuation of the handle assembly;
   a brake release mechanism operable to release the brake upon manual pulling of the handle portions together;
   a yoke fitted over the sheath;
   the sprung element attached to the yoke;
   the sprung element imparting a pulling force on the yoke, thereby placing the yoke in a tilted position relative to the sheath; and
   wherein when the yoke is in the tilted position, the brake release mechanism engages the brake element so that the brake element prevents the drive assembly from providing the retraction assistance force.

14. An introducer assembly comprising:
   a carrier element having a distal end and a proximal end;
   a sheath overlying the carrier element and having a distal end and a proximal end;
   a first handle portion attached to the proximal end of the sheath and a second handle portion attached to the proximal end the carrier element; and
   a drive assembly coupled between the first handle portion and the second handle portion and operable to provide a retraction assistance force pulling the first handle portion and the second handle portion together;
   wherein the drive assembly includes:
   a yoke fitted over the sheath;
   a sprung element attached to the yoke;
   a brake element releasably engaged to the sprung element;
   a brake release element attached to the yoke and releasably engaged to the brake element;
   the sprung element imparting a pulling force on the yoke, thereby placing the yoke in a tilted position relative to the sheath; and
   wherein when the yoke is in the tilted position, the brake release element engages the brake element so that the brake element prevents the drive assembly from providing the retraction assistance force.

15. An introduce assembly according to claim 14, further comprising a gripping element attached to the yoke; and
   wherein pulling the gripping element places the yoke in an untilted position, allowing the drive assembly to provide the retraction assistance force.

16. An introducer assembly according to claim 14, wherein the sprung element further comprises a spool element.

17. An introducer assembly according to claim 16, wherein the spool element is a toothed spool; and
wherein the brake element is releasably engaged to the toothed spool.

18. An introducer assembly according to claim 14, wherein a spring is held at one end by the yoke and at the other end against the first handle potion.

19. An introduce assembly according to claim 14, wherein the drive assembly further comprises a speed control mechanism.

20. An introducer assembly according to claim 19, wherein the speed control mechanism further comprises a friction element for applying friction to the drive assembly thereby to control its speed of movement.

* * * * *